(12) United States Patent
Kato (10) Patent No.: US 10,682,504 B2
(45) Date of Patent: Jun. 16, 2020

(54) MICRONEEDLE AND METHOD FOR MANUFACTURING MICRONEEDLE

(71) Applicant: TOPPAN PRINTING CO., LTD., Taito-ku (JP)

(72) Inventor: Hiroyuki Kato, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 423 days.

(21) Appl. No.: 15/003,366

(22) Filed: Jan. 21, 2016

(65) Prior Publication Data

US 2016/0136408 A1 May 19, 2016

Related U.S. Application Data

(63) Continuation-in-part of application No. PCT/JP2014/068398, filed on Jul. 10, 2014.

(30) Foreign Application Priority Data

Jul. 22, 2013 (JP) .................. 2013-151573

(51) Int. Cl.
*A61M 37/00* (2006.01)
*B29C 39/00* (2006.01)
(Continued)

(52) U.S. Cl.
CPC ....... *A61M 37/0015* (2013.01); *B29C 39/003* (2013.01); *B29C 39/025* (2013.01);
(Continued)

(58) Field of Classification Search
CPC ........ A61M 2205/0244; A61M 31/002; A61M 37/0015; A61M 2037/0023;
(Continued)

(56) References Cited

U.S. PATENT DOCUMENTS

2002/0082543 A1* 6/2002 Park .................. A61B 5/1411
604/21
2002/0164352 A1* 11/2002 Donatini ............. A61K 31/722
424/195.15
(Continued)

FOREIGN PATENT DOCUMENTS

JP 2011-224332 A 11/2011
JP 2013-527853 A 7/2013
WO WO 2008/020632 A1 2/2008

OTHER PUBLICATIONS

International Search Report dated Oct. 21, 2014 in PCT/JP2014/068398, filed Jul. 10, 2014.
(Continued)

*Primary Examiner* — Bhisma Mehta
*Assistant Examiner* — William R Frehe
(74) *Attorney, Agent, or Firm* — Oblon, McClelland, Maier & Neustadt, L.L.P.

(57) ABSTRACT

A microneedle includes a substrate, and projections which extend from a surface of the substrate. Each of the projections includes layers separated from each other in a direction in which the projection extends. The layers include a first layer which contains a polymer which is soluble in water and poorly soluble in oil and a second layer which contains a polymer that is soluble in oil. The first layer and the second layer are adjacent to each other and are formed in the order of the first layer and the second layer from the projection to the substrate.

17 Claims, 3 Drawing Sheets

(51) Int. Cl.
  *B29C 39/02* (2006.01)
  *B29K 67/00* (2006.01)
  *B29L 31/00* (2006.01)

(52) U.S. Cl.
  CPC .............. *A61M 2037/0023* (2013.01); *A61M 2037/0046* (2013.01); *A61M 2037/0053* (2013.01); *B29K 2067/046* (2013.01); *B29K 2995/0062* (2013.01); *B29L 2031/753* (2013.01); *B29L 2031/756* (2013.01)

(58) Field of Classification Search
  CPC .. A61M 2037/0046; A61M 2037/0053; A61M 2037/0061; A61K 9/0097; B81C 1/00111; B81B 2201/055
  See application file for complete search history.

(56) References Cited

U.S. PATENT DOCUMENTS

| | | | | |
|---|---|---|---|---|
| 2002/0177858 | A1* | 11/2002 | Sherman | A45D 26/0004 606/131 |
| 2008/0200883 | A1 | 8/2008 | Tomono | |
| 2008/0208134 | A1 | 8/2008 | Tomono | |
| 2008/0269685 | A1* | 10/2008 | Singh | A61K 9/0021 604/173 |
| 2009/0099537 | A1* | 4/2009 | DeVoe | A61M 37/0015 604/272 |
| 2009/0292254 | A1 | 11/2009 | Tomono | |
| 2009/0292255 | A1 | 11/2009 | Tomono | |
| 2012/0027810 | A1* | 2/2012 | Chen | A61M 37/0015 424/400 |
| 2012/0130306 | A1* | 5/2012 | Terahara | A61K 9/0021 604/46 |
| 2013/0072902 | A1* | 3/2013 | Takada | A61M 37/0015 604/506 |
| 2015/0030642 | A1* | 1/2015 | Wu | A61K 9/0021 424/400 |

OTHER PUBLICATIONS

Office Action dated Aug. 1, 2018 in corresponding Japanese Patent Application No. 2015-528222 (with English Translation), 4 pages.

* cited by examiner

MICRONEEDLE AND METHOD FOR MANUFACTURING MICRONEEDLE

CROSS-REFERENCE TO RELATED APPLICATIONS

The present application is a continuation-in-part of International Application No. PCT/JP2014/068398, filed Jul. 10, 2014, which is based upon and claims the benefits of priority to Japanese Application No. 2013-151573, filed Jul. 22, 2013. The entire contents of these applications are incorporated herein by reference.

BACKGROUND OF THE INVENTION

Field of the Invention

The technique of the present disclosure relates to microneedles having a plurality of projections which extend from the surface of substrate and a method for manufacturing the microneedles.

Discussion of the Background

Use of microneedles is known as a technique for transdermal administration of a substance such as a drug into the body. The microneedle includes a plurality of projections in the form of needles on the surface of substrate. In the administration method using a microneedle, the projections pierce the skin when the substrate is pressed against the skin so that the substance is delivered into the body through the holes formed by the projections.

The microneedle is made of, for example, a material containing water soluble polymer as a main component as described in PTL 1. When pierced into the skin, the microneedle containing water soluble polymer as a main component is dissolved in the water contained in the skin. As the microneedle containing water soluble polymer and a substance to be delivered are dissolved in the skin, the substance to be delivered is penetrated into the body.

The microneedles described above are manufactured, for example, by supplying a solution of a material which forms the microneedle into a mold having the shape corresponding to the shape of the microneedle and solidifying the solution in the mold.

PTL 1: WO 2008/020632

SUMMARY OF THE INVENTION

According to one aspect of the present invention, a microneedle includes a substrate, and projections which extend from a surface of the substrate. Each of the projections has layers separated from each other in a direction in which the projection extends. The layers include a first layer and a second layer which are adjacent to each other and formed in an order of the first layer and the second layer from the projection to the substrate. The first layer includes a polymer which is soluble in water and poorly soluble in oil, and the second layer includes a polymer soluble in oil.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

The embodiments will now be described with reference to the accompanying drawings, wherein like reference numerals designate corresponding or identical elements throughout the various drawings.

With reference to FIGS. 1 to 9, a microneedle according an embodiment of the present disclosure will be described.

Structure of Microneedle

Figure 1:
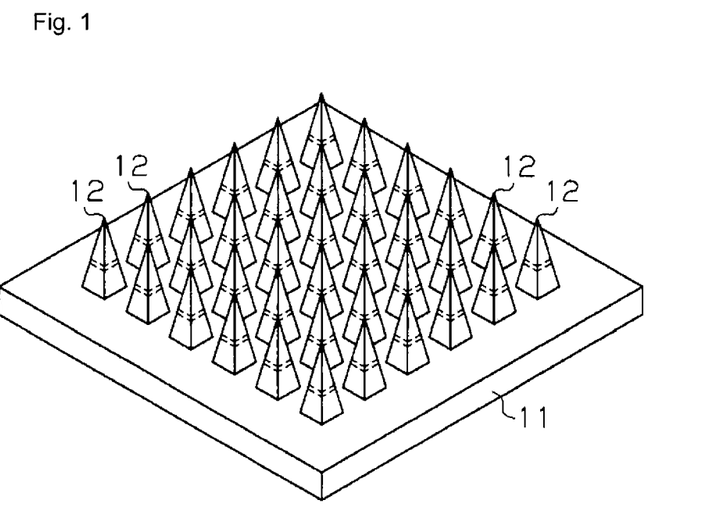
FIG. 1 is a perspective view which shows a perspective structure of a microneedle according to one embodiment of the technique of the present disclosure.
Figure 2:
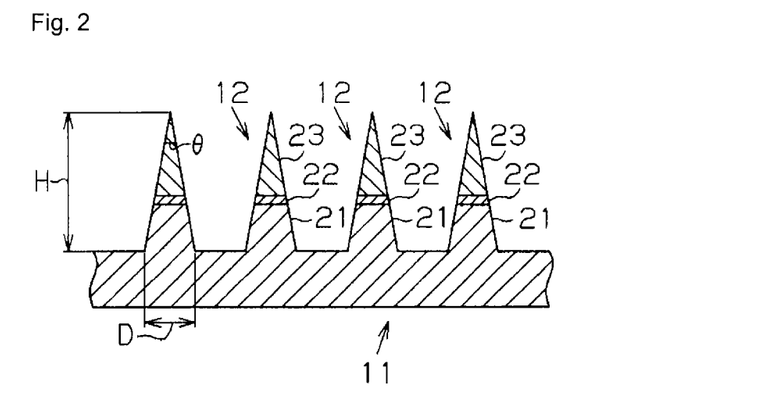
FIG. 2 is a sectional view which shows part of a cross sectional structure of the microneedle of FIG. 1.

With reference to FIGS. 1 and 2, a structure of the microneedle will be described.

As shown in FIG. 1, the microneedle includes a substrate 11 and a plurality of projections 12 which extend from an upper surface of the substrate 11. The under surfaces of the projections 12 are integrally formed with the upper surface of the substrate 11 such that the substrate 11 supports the respective proximal ends of a plurality of projections 12.

The substrate 11 may be in the form of a flat plate, a curved plate or a cuboid shape. The substrate 11 is preferably formed as a flat plate since this can easily provide flexibility of the substrate 11.

The projection 12 may be in the shape of a pyramid or a conical shape. The projection 12 may also be in the shape which does not have a pointed tip, for example, a cylinder or a prism. Alternatively, the projection 12 may be in the shape of a combination of two solids, for example, a cone stacked on a cylinder. In other words, the projection 12 may be in any shape that can pierce the skin. Any number of one or more projections 12 may be provided.

A plurality of projections 12 may be arranged regularly or irregularly on the surface of the substrate 11. Further, a plurality of projections 12 may be positioned in groups at a plurality of positions on the upper surface of the substrate 11. For example, a plurality of projections 12 may be arranged in a matrix or a concentric pattern.

When the microneedle is used, the lower surface of the substrate 11 is pressed against the skin with the tips of the projections 12 facing the skin. The microneedle may be provided with an applicator that guides the position or orientation of the microneedle.

As shown in FIG. 2, the projection 12 preferably has a height H of 10 μm or more and 1000 μm or less. The height H of the projection 12 is a length from the upper surface of the substrate 11 to the tip of the projection 12. The height H of the projection 12 is decided depending on the depth of a hole that needs to be formed. When a hole is desired to be formed in the human skin so that the tip of the hole is in the stratum corneum, the height H is preferably 10 μm or more and 300 μm or less, and more preferably, 30 μm or more and 200 μm or less. When the tip of the hole is desired to penetrate through the stratum corneum and not to reach the nerve plexus, the height H is preferably 200 μm or more and 700 μm or less, preferably 200 μm or more and 500 μm or less, and more preferably 200 μm or more and 300 μm or less. When the tip of the hole is desired to reach the dermis, the height H is 200 μm or more and 500 μm or less. When the depth of the hole is desired to reach the dermis, the height H is preferably 200 μm or more and 300 μm or less.

The projection 12 has a width D, which is the maximum length of the projection 12 in the direction parallel to the upper surface of the substrate 11. The projection 12 preferably has the width D of 1 μm or more and 300 μm or less. For example, when the projection 12 has a quadrangular pyramid shape or a quadrangular prism shape, a square is formed on the upper surface of the substrate 11 as an outline of the bottom of the projection 12. A diagonal length of the square defined by the bottom of the projection 12 is the width D of the projection 12. For example, when the projection 12 has a conical shape or a cylindrical shape, a diameter of the circle defined by the bottom of the projection 12 is the width D of the projection 12.

An aspect ratio A (A=H/D) of the projection 12, which is a ratio of the height H to the width D, is preferably 1 or more and 10 or less.

When the projection 12 is formed to have a pointed tip so as to form a hole which penetrates through the stratum corneum, the projection 12 preferably has a tip angle θ of 5° or more and 30° or less, and more preferably 10° or more and 20° or less. The tip angle θ is the maximum angle formed by the tip of the projection 12 in a cross section perpendicular to the upper surface of the substrate 11. For example, when projection 12 has a quadrangular pyramid shape, the tip angle θ of the projection 12 is an apex angle of an isosceles triangle having a base made by a diagonal line of the square of the bottom of the projection 12 and an apex made by an apex of the regular quadrangular pyramid.

The width D, the aspect ratio A, and the apex angle θ of the projection 12 are decided depending on a volume necessary for the hole to be formed. When the height H, the width D, the aspect ratio A and the apex angle θ are in the above range, the shape of the projection 12 is suitable for forming a hole in the skin.

The microneedle is made up of a plurality of layers which are separated from each other in the extending direction of the projection 12. A plurality of layers includes a distal layer 23 which is an example of a first layer that contains polymer that is soluble in water and poorly soluble in oil, and an intermediate layer 22 which is an example of a second layer that contains polymer that is soluble in oil. The distal layer 23 is located closer to the tip of the projection 12 than the intermediate layer 22 is, and the distal layer 23 and the intermediate layer 22 are adjacent to each other. The microneedle preferably includes a proximal layer 21 which is an example of a third layer as one of a plurality of layers. The following describes an example of the microneedle made up of the proximal layer 21, the intermediate layer 22 and the distal layer 23.

Water solubility is a property that 2 g or more of a substance dissolves in 100 g water at room temperature under atmospheric pressure, while poor water solubility is a property that 2 g or more of a substance does not dissolve in 100 g water at room temperature under atmospheric pressure. Oil solubility is a property that 2 g or more of a substance dissolves in 100 g ethanol at room temperature under atmospheric pressure, while poor oil solubility is a property that 2 g or more of a substance does not dissolve in 100 g ethanol at room temperature under atmospheric pressure.

The proximal layer 21 includes a proximal end of the projection 12 and the substrate 11. The distal layer 23 includes the tip of the projection 12. The intermediate layer 22 includes part of the projection 12, and is interposed between the proximal layer 21 and the distal layer 23. That is, the distal layer 23, the intermediate layer 22 and the proximal layer 21 are disposed in this order in the direction which extends from the projection 12 to the substrate 11.

In the height direction of the projection 12, the thickness of the intermediate layer 22 is smaller than the thickness of the proximal layer 21, and is smaller than the thickness of the distal layer 23. The thickness of the intermediate layer 22 may be any thickness as long as it can separate the proximal layer 21 and the distal layer 23, and it is more preferable that the intermediate layer 22 has a smaller thickness.

The proximal layer 21 is made of a material that contains polymer that is soluble in water and poorly soluble in oil. Preferably, the polymer contained in the proximal layer 21 is one selected from a group consisting of carboxymethyl cellulose, hydroxypropyl cellulose, chitosan salt, chitosan succinamide, alginate, pullulan, dextran and chondroitin sulfate.

The intermediate layer 22 is made of a material that contains polymer that is poorly soluble in water and soluble in oil. Preferably, the polymer contained in the intermediate layer 22 is ethyl cellulose. Propyl cellulose may be used instead of ethyl cellulose. Preferably, the polymer contained in the intermediate layer 22 is, for example, ethanol or isopropyl alcohol, which is dissolved in a solvent having less effect on the human body. Polylactic acid may be used instead of ethyl cellulose.

The distal layer 23 is made of a material that includes polymer that is soluble in water and poorly soluble in oil and a substance to be delivered into the body. In the distal layer 23, the polymer serves as a base, while the substance to be delivered is contained in the distal layer 23 while carried by the polymer. When the distal layer 23 is dissolved in the water contained in the skin, the substance to be delivered contained in distal layer 23 is diffused into the body.

Preferably, the polymer contained in the distal layer 23 is one selected from a group consisting of carboxymethyl cellulose, hydroxypropyl cellulose, chitosan salt, chitosan succinamide, alginate, pullulan, dextran and chondroitin sulfate. Polymer contained in the distal layer 23 may be the same or different from that contained in the proximal layer 21.

The substance to be delivered may be pharmacological active agents or cosmetic compositions. The types of substance to be delivered may be selected depending on the intended purpose.

The pharmacological active agents may include, for example, vaccines against influenza, analgesics for cancer patients, biologic agents, gene therapy agents, injection agents, oral agents or skin applying agents. In transdermal administration using a microneedle, a drug is administered into a hole formed in the skin. Accordingly, transdermal administration using a microneedle may be applied to administration of pharmacological active agents which need hypodermic injection in addition to the conventional transdermal administration of pharmacological active agents. In particular, since transdermal administration using a microneedle is painless, it is suitable for administration of injection agents such as vaccines to children. Further, since there is no need of swallowing a medication in drug administration, transdermal administration using a microneedle is suitable for use with children who have difficulty in swallowing an oral medication.

The cosmetic compositions are compositions used for cosmetics or beauty products. For example, the cosmetic compositions may include moisturizing agents, coloring materials, fragrances, and biologically active substances that express beauty effects such as beneficial effects for wrinkles, acne, stretch marks and the like and mitigating effects on hair loss. When an aromatic material is used as a substance to be delivered, a favorable fragrance can be added to the microneedle. This is suitable for use as a beauty product.

The ratio of the substance to be delivered contained in the distal layer 23 and the water soluble polymer is decided depending on the amount needed to be delivered into the body and the amount of the water soluble polymer needed to form the distal layer 23.

After the microneedle is pierced into the skin, the proximal layer 21 and the distal layer 23 are dissolved in the water contained in the skin. The intermediate layer 22 is degraded by metabolism or excreted along with cornification.

Method for Manufacturing Microneedle

With reference to FIGS. 3 to 9, a method for manufacturing microneedle will be described. In FIGS. 3 to 9, the number of projections 12 of the microneedle is shown in a simplified form.

The method for manufacturing a microneedle includes a process of forming a first layer by supplying a solution in which a material containing polymer that is soluble in water and poorly soluble in oil is dissolved in water into a mold and by solidifying the supplied solution, and a process of forming a second layer by supplying a solution in which a material containing polymer that is soluble in oil is dissolved in organic solvent onto the first layer in the mold and by solidifying the supplied solution. The following describes one example of a method for manufacturing a microneedle, which is a method for manufacturing a microneedle made up of the proximal layer 21, the intermediate layer 22 and the distal layer 23.

<Process of Forming a Mold>

Figure 3:
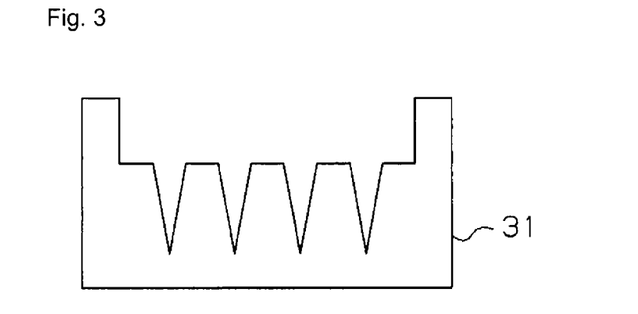
FIG. 3 is a schematic view which shows a manufacturing process of the microneedle of FIG. 1, in which a manufactured mold is illustrated.

As shown in FIG. 3, in a process of forming a mold, a mold 31 having recesses which correspond to the shape of the microneedle is formed. First, an original plate of the microneedle is prepared. The shape of the original plate defines the shape of the microneedle to be manufactured. The original plate is manufactured by a method appropriate for the shape of the microneedle. The original plate is formed, for example, by using a micromachining technique. The micromachining technique may include, for example, lithography, wet etching, dry etching, sandblasting, laser machining and precision machining.

Then, the original plate is used to form the mold 31. The mold 31 is formed by using a known feature replication method. The feature replication method may include, for example, forming a Ni-based mold by using Ni-electrocasting, transferring the shape using molten resin and the like.

<Process of Preparing a Distal Layer Forming Material>

Figure 4:
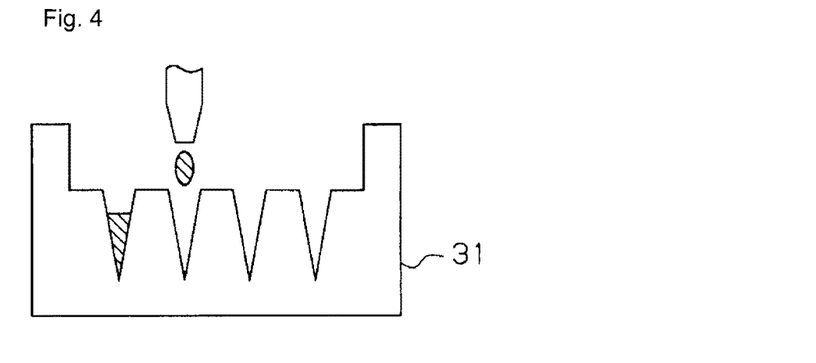
FIG. 4 is a schematic view which shows a manufacturing process of the microneedle of FIG. 1, in which a supplying process of a distal layer forming solution is illustrated.

In a process of preparing a distal layer forming material, the distal layer forming solution which contains a forming material for the distal layer is prepared. The distal layer forming solution is prepared by allowing polymer that is soluble in water and poorly soluble in oil and the substance to be delivered to dissolve in water. The distal layer forming solution preferably has a fluidity of such an extent that allows it to be supplied into the mold 31.

<Process of Supplying a Distal Layer Forming Solution>

As shown in FIG. 4, in a process of supplying a distal layer forming solution, the distal layer forming solution is supplied into the mold 31. The amount of the distal layer forming solution to be supplied is decided depending on the thickness of the distal layer 23. The distal layer forming solution is supplied into the mold 31 in a manner suitable for the size and shape of the mold 31. The methods for supplying the distal layer forming solution into the mold 31 may include, for example, a spin coating method, a method using a dispenser, a casting method and an ink-jet method. Further, the distal layer forming solution may be supplied with the mold 31 placed under a reduced pressure or vacuum.

<Process of Solidifying a Distal Layer Forming Solution>

Figure 5:
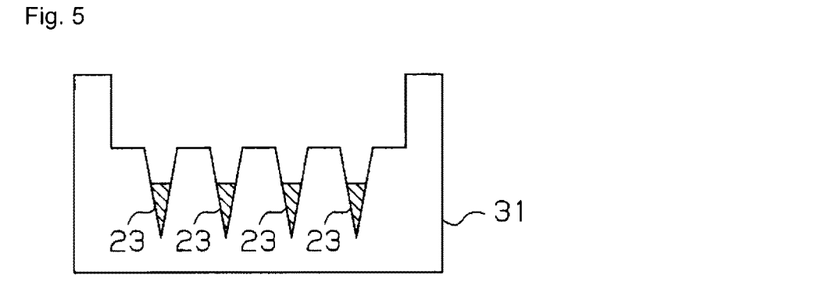
FIG. 5 is a schematic view which shows a manufacturing process of the microneedle of FIG. 1, in which a solidifying process of the distal layer forming solution is illustrated.

As shown in FIG. 5, in a process of solidifying a distal layer forming solution, the distal layer forming solution supplied in the mold 31 is dried and solidified. The distal layer forming solution may be dried at room temperature or may be dried under a heated environment. By drying the distal layer forming solution under a heated environment, the time required for the solidifying process can be reduced. Preferably, the heating temperature is of an extent that suppresses boiling of the solution in order to prevent air bubbles from being generated in the microneedle. Specifically, the heating temperature is preferably 50° or more and 90° or less. The heating method may be a known heating method. For example, the mold 31 in which the distal layer forming solution is supplied is placed on a heated hotplate to heat the distal layer forming solution. When the distal layer forming solution is solidified, the distal layer 23 is formed.

<Process of Preparing an Intermediate Layer Forming Material>

Figure 6:
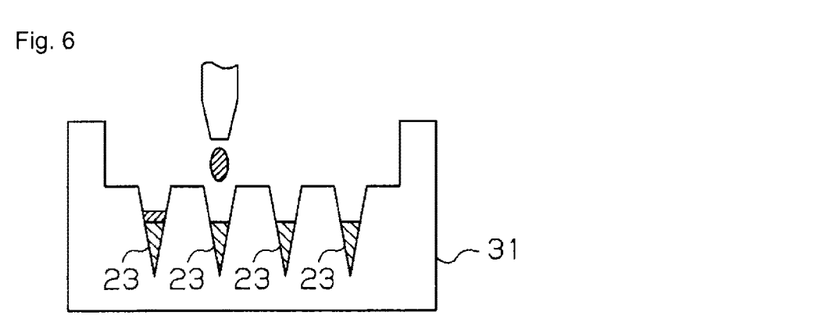
FIG. 6 is a schematic view which shows a manufacturing process of the microneedle of FIG. 1, in which a supplying process of an intermediate layer forming solution is illustrated.

In a process of preparing an intermediate layer forming material, the intermediate layer forming solution which contains a forming material for the intermediate layer is prepared. The intermediate layer forming solution is prepared by allowing polymer that is poorly soluble in water and soluble in oil to dissolve in a solvent such as an organic solvent. The solvent is such that the polymer poorly soluble in oil is less soluble in the solvent. The intermediate layer forming solution preferably has a fluidity of such an extent that allows it to be supplied into the mold 31.

<Process of Supplying an Intermediate Layer Forming Solution>

As shown in FIG. 6, in a process of supplying an intermediate layer forming solution, the intermediate layer forming solution is supplied into the mold 31. The intermediate layer forming solution is supplied on the distal layer 23 formed in the mold 31. The amount of the intermediate layer forming solution to be supplied is decided depending on the thickness of the intermediate layer 22. The intermediate layer forming solution is supplied into the mold 31 in a manner suitable for the size and shape of the mold 31. The methods for supplying the intermediate layer forming solution into the mold 31 may be various methods including the same methods as those described for supplying the distal layer forming solution. The method for supplying the intermediate layer forming solution may be the same as or different from the method for supplying the distal layer forming solution.

\<Process of Solidifying an Intermediate Layer Forming Solution\>

Figure 7:
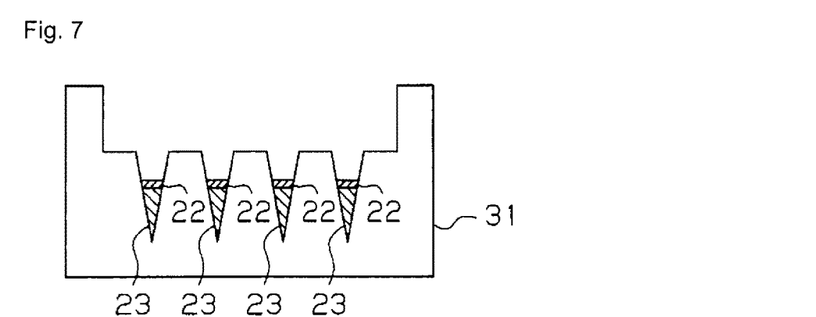
FIG. 7 is a schematic view which shows a manufacturing process of the microneedle of FIG. 1, in which a solidifying process of the intermediate layer forming solution is illustrated.

As shown in FIG. 7, in a process of solidifying an intermediate layer forming solution, the intermediate layer forming solution supplied in the mold 31 is dried and solidified. The intermediate layer forming solution may be dried at room temperature or may be dried under a heated environment. By drying the intermediate layer forming solution under a heated environment, the time required for the solidifying process can be reduced. Preferably, the heating temperature is of an extent that suppresses boiling of the solution in order to prevent air bubbles from being generated in the microneedle. The heating method may be a known heating method such as heating by using a hotplate. When the intermediate layer forming solution is solidified, the intermediate layer 22 is formed.

\<Process of Preparing a Proximal Layer Forming Material\>

Figure 8:
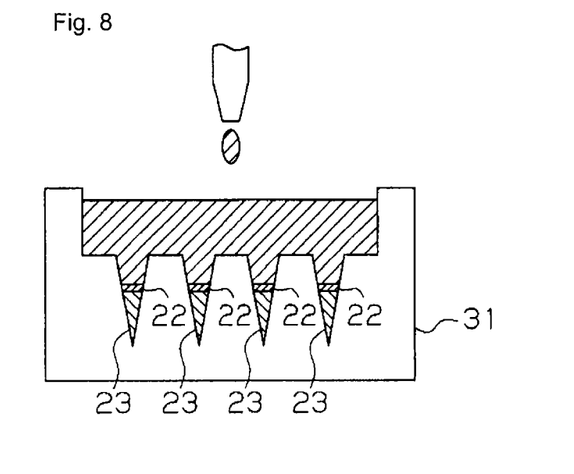
FIG. 8 is a schematic view which shows a manufacturing process of the microneedle of FIG. 1, in which a supplying process of a proximal layer forming solution is illustrated.

In a process of preparing a proximal layer forming material, the proximal layer forming solution which contains a forming material for the proximal layer is prepared. The proximal layer forming solution is prepared by allowing polymer that is soluble in water and poorly soluble in oil to dissolve in water. The proximal layer forming solution preferably has a fluidity of such an extent that allows it to be supplied into the mold 31.

\<Process of Supplying a Proximal Layer Forming Solution\>

As shown in FIG. 8, in a process of supplying a proximal layer forming solution, the proximal layer forming solution is supplied into the mold 31. The proximal layer forming solution is supplied on the intermediate layer 22 formed in the mold 31. The amount of the proximal layer forming solution to be supplied is decided depending on the thickness of the proximal layer 21. The proximal layer forming solution is supplied into the mold 31 in a manner suitable for the size and shape of the mold 31. The methods for supplying the proximal layer forming solution into the mold 31 may include the same methods as those described for supplying the distal layer forming solution. The method for supplying the proximal layer forming solution may be the same as or different from the method for supplying the distal layer forming solution and the intermediate layer forming solution.

\<Process of Solidifying a Proximal Layer Forming Solution\>

Figure 9:
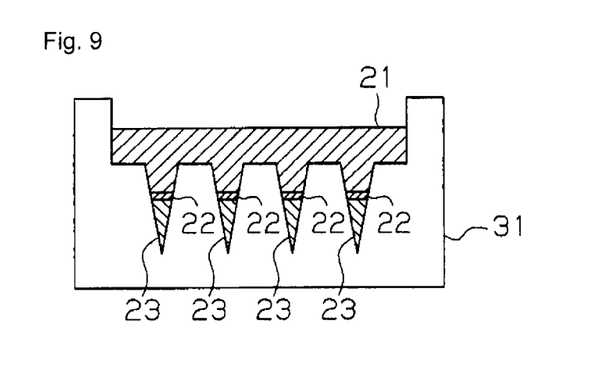
FIG. 9 is a schematic view which shows a manufacturing process of the microneedle of FIG. 1, in which a solidifying process of the proximal layer forming solution is illustrated.

As shown in FIG. 9, in a process of solidifying a proximal layer forming solution, the proximal layer forming solution supplied in the mold 31 is dried and solidified. The proximal layer forming solution may be dried at room temperature or may be dried under a heated environment. By drying the proximal layer forming solution under a heated environment, the time required for the solidifying process can be reduced. Preferably, the heating temperature is of an extent that suppresses boiling of the solution in order to prevent air bubbles from being generated in the microneedle. Specifically, the heating temperature is preferably 50° or more and 90° or less. The heating method may be a known heating method such as heating by using a hotplate. When the proximal layer forming solution is solidified, the proximal layer 21 is formed.

\<Process for Removing a Microneedle\>

In a process of removing a microneedle, a resultant product which is solidified is removed from the mold 31. The resultant product which is removed from the mold 31 is the microneedle. The process for removing a microneedle may include, for example, separating a resultant product from the mold 31 with physical force, and selectively dissolving the mold 31 by using chemical properties.

Effects

The effects of the microneedle according to the present embodiment will be described.

In the manufacturing process of the microneedle according to the present embodiment, after the solution in which the polymer poorly soluble in oil dissolves is solidified to form the distal layer 23, the solution for forming the intermediate layer 22 is supplied on the distal layer 23. Since the polymer contained in the intermediate layer 22 is soluble in oil, the polymer poorly soluble in oil is less soluble in the solvent of the intermediate layer forming solution in which the polymer soluble in oil dissolves. Accordingly, when the intermediate layer forming solution is supplied on the distal layer 23, the polymer contained in the solidified distal layer 23 can be prevented from being eluted into the intermediate layer forming solution.

Furthermore, after the solution in which the polymer poorly soluble in water dissolves is solidified to form the intermediate layer 22, the solution for forming the proximal layer 21 is supplied on the intermediate layer 22. Since the polymer contained in the proximal layer 21 is soluble in water, the polymer poorly soluble in water is less soluble in the solvent of the proximal layer forming solution in which the polymer poorly soluble in water dissolves. Accordingly, when the proximal layer forming solution is supplied on the intermediate layer 22, the polymer contained in the solidified intermediate layer 22 can be prevented from being eluted into the proximal layer forming solution.

As a result, the polymer contained in each layer can be prevented from being mixed with that contained in the adjacent layer. In other words, in the method for manufacturing microneedle according to the present embodiment, the solution containing the forming material of each layer is supplied and solidified subsequently from the layer on the tip of the projection 12. In the microneedle manufactured by the above method, the polymer contained in the layer formed earlier is prevented from easily dissolving in the solvent in which the polymer contained in the layer formed later easily dissolves. Accordingly, the polymer contained in each layer can be prevented from being mixed into the adjacent layer.

Further, since the polymer which serves as a base in the distal layer 23 can be prevented from being mixed into the adjacent intermediate layer 22, the substance to be delivered contained in the distal layer 23 is prevented from being mixed along with the polymer into the intermediate layer 22. Accordingly, since the substance to be delivered can be intensively disposed in the distal layer 23 that is inserted into the skin to a deep position, the substance to be delivered can be slowly released from a position deep in the skin. Further, since the substance to be delivered can be prevented from being diffused in the substrate 11 that is not inserted into the skin, use of a substance which is unnecessary to be delivered can be prevented. Further, when the substance to be delivered is soluble in water and poorly soluble in oil, the substance to be delivered contained in the distal layer 23 is further prevented from being mixed into the intermediate layer 22.

In the conventional case in which a plurality of layers that contain different types of water soluble polymers are stacked or a plurality of layers that contain water soluble polymers with different content percentages are stacked, it is difficult to prevent polymer in each layer from being mixed into another layer. In this embodiment, however, the polymer contained in each of the proximal layer 21 and the distal layer 23 can be prevented from being mixed, and varying the types or the content percentages of the water soluble polymers contained in each of the proximal layer 21 and the distal layer 23 allows for two types of layers to perform their functions independently. The thickness of the intermediate layer 22 may be any thickness as long as it can separate the proximal layer 21 and the distal layer 23. The intermediate layer 22 may have a thickness smaller than that of the proximal layer 21 and the distal layer 23. Accordingly, if the thickness of the intermediate layer 22 increases compared with the conventional case, the thickness of the other layers or the amount of the substance to be delivered and the polymer is less affected by the increase.

EXAMPLE

Specific examples of the above described microneedle will be described.

Case 1

Example 1, Example 2, Example 3 and Example 4 show manufacturing of a three layered microneedle made up of a distal layer, an intermediate layer and a proximal layer will be described. Further, Reference example 1 shows manufacturing of another example of the microneedle of Example 1 which does not includes the intermediate layer.

Example 1

Manufacturing of Mold

An original plate for the microneedle was formed by micromachining a silicon substrate. Thirty six projections were arrayed on a substrate in a matrix of 6 rows by 6 columns with a pitch of 1 mm, each having the shape of a regular quadrangular pyramid (height: 150 μm, bottom: 60 μm×60 μm).

The original plate for the microneedle was coated with a nickel film by plating in the thickness of 500 μm. Then, the original plate for the microneedle made of silicon was wet-etched with potassium hydroxide solution of weight percent concentration of 30% which was heated at a temperature of 90° C. to manufacture a mold made of nickel.

<Manufacturing of Distal Layer>

Chitosan succinamide was dissolved in water to prepare the distal layer forming solution. Evans Blue was added to the distal layer forming solution so as to have a 1% concentration relative to the distal layer forming solution. Then, the distal layer forming solution was injected into the recess of the mold by using an inkjet method. The mold in which the distal layer forming solution was supplied was heated at a temperature of 90° C. for a period of 10 minutes so as to dry and solidify the distal layer forming solution. A hotplate was used as a heat source for heating.

<Manufacturing of Intermediate Layer>

Ethyl cellulose was dissolved in ethanol to prepare the intermediate layer forming solution. Then, the intermediate layer forming solution was injected into the mold in which the distal layer was formed by using an inkjet method. The mold to which the intermediate layer forming solution was supplied was heated at a temperature of 40° C. for a period of 10 minutes so as to dry and solidify the intermediate layer forming solution. A hotplate was used as a heat source for heating.

<Manufacturing of Proximal Layer>

Chitosan succinamide was dissolved in water to prepare the proximal layer forming solution. Rhodamine B was added to the proximal layer forming solution so as to have a 1% concentration relative to the distal layer forming solution. Then, the proximal layer forming solution was injected into the mold in which the distal layer and the intermediate layer were formed by using a spin coating method. The mold in which the proximal layer forming solution was supplied was heated at a temperature of 90° C. for a period of 10 minutes so as to dry and solidify the proximal layer forming solution. A hotplate was used as a heat source for heating.

<Removal of Microneedle>

The resultant product which was solidified was removed from the mold to obtain the microneedle of Example 1.

<Observation Result>

In the microscopic observation of the microneedle of Example 1, the distal layer and the proximal layer were clearly confirmed. In the microneedle of Example 1, a three layered structure made up of a stack of the layer containing chitosan succinamide, the layer containing ethyl cellulose, and the layer containing chitosan succinamide were formed.

Example 2

Manufacturing of Mold

An original plate for the microneedle was formed by micromachining a silicon substrate in the same manner as that of Example 1. Then, a mold made of nickel is formed by plating in the same manner as that of Example 1.

Manufacturing of Distal Layer

Carboxymethyl cellulose was dissolved in water to prepare the distal layer forming solution. Evans Blue was added to the distal layer forming solution so as to have a 1% concentration relative to the distal layer forming solution. Then, the distal layer forming solution was injected into the recess of the mold by using an inkjet method. The mold in which the distal layer forming solution was supplied was heated at a temperature of 90° C. for a period of 10 minutes so as to dry and solidify the distal layer forming solution. A hotplate was used as a heat source for heating.

<Manufacturing of Intermediate Layer>

Ethyl cellulose was dissolved in ethanol to prepare the intermediate layer forming solution. Then, the intermediate layer forming solution was injected into the mold in which the distal layer was formed by using an inkjet method. The mold to which the intermediate layer forming solution was supplied was heated at a temperature of 40° C. for a period of 10 minutes so as to dry and solidify the intermediate layer forming solution. A hotplate was used as a heat source for heating.

<Manufacturing of Proximal Layer>

Hydroxypropyl cellulose was dissolved in water to prepare the proximal layer forming solution. Rhodamine B was added to the proximal layer forming solution so as to have a 1% concentration relative to the distal layer forming solution. Then, the proximal layer forming solution was injected into the mold in which the distal layer and the intermediate layer were formed by using a spin coating method. The mold in which the proximal layer forming solution was supplied was heated at a temperature of 90° C. for a period of 10 minutes so as to dry and solidify the proximal layer forming solution. A hotplate was used as a heat source for heating.

<Removal of Microneedle>

The resultant product which was solidified was removed from the mold to obtain the microneedle of Example 2.

<Observation Result>

In the microscopic observation of the microneedle of Example 2, the distal layer and the proximal layer were clearly confirmed. In the microneedle of Example 2, a three layered structure made up of a stack of the layer containing carboxymethyl cellulose, the layer containing ethyl cellulose, and the layer containing hydroxypropyl cellulose were formed.

Example 3

Manufacturing of Mold

An original plate for the microneedle was formed by micromachining a silicon substrate in the same manner as that of Example 1. Then, a mold made of nickel is formed by plating in the same manner as that of Example 1.
<Manufacturing of Distal Layer>

Chitosan succinamide was dissolved in water to prepare the distal layer forming solution. Evans Blue was added to the distal layer forming solution so as to have a 1% concentration relative to the distal layer forming solution. Then, the distal layer forming solution was injected into the recess of the mold by using an inkjet method. The mold in which the distal layer forming solution was supplied was heated at a temperature of 90° C. for a period of 10 minutes so as to dry and solidify the distal layer forming solution. A hotplate was used as a heat source for heating.
<Manufacturing of Intermediate Layer>

Propyl cellulose was dissolved in ethanol to prepare the intermediate layer forming solution. Then, the intermediate layer forming solution was injected into the mold in which the distal layer was formed by using an inkjet method. The mold to which the intermediate layer forming solution was supplied was heated at a temperature of 40° C. for a period of 10 minutes so as to dry and solidify the intermediate layer forming solution. A hotplate was used as a heat source for heating.
<Manufacturing of Proximal Layer>

Chitosan succinamide was dissolved in water to prepare the proximal layer forming solution. Rhodamine B was added to the proximal layer forming solution so as to have a 1% concentration relative to the distal layer forming solution. Then, the proximal layer forming solution was injected into the mold in which the distal layer and the intermediate layer were formed by using a spin coating method. The mold in which the proximal layer forming solution was supplied was heated at a temperature of 90° C. for a period of 10 minutes so as to dry and solidify the proximal layer forming solution. A hotplate was used as a heat source for heating.
<Removal of Microneedle>

The resultant product which was solidified was removed from the mold to obtain the microneedle of Example 1.
<Observation Result>

In the microscopic observation of the microneedle of Example 3, the distal layer and the proximal layer were clearly confirmed. In the microneedle of Example 1, a three layered structure made up of a stack of the layer containing chitosan succinamide, the layer containing propyl cellulose, and the layer containing chitosan succinamide were formed.

Example 4

Manufacturing of Mold

An original plate for the microneedle was formed by micromachining a silicon substrate in the same manner as that of Example 1. Then, a mold made of nickel is formed by plating in the same manner as that of Example 1.
<Manufacturing of Distal Layer>

Chitosan succinamide was dissolved in water to prepare the distal layer forming solution. Evans Blue was added to the distal layer forming solution so as to have a 1% concentration relative to the distal layer forming solution. Then, the distal layer forming solution was injected into the recess of the mold by using an inkjet method. The mold in which the distal layer forming solution was supplied was heated at a temperature of 90° C. for a period of 10 minutes so as to dry and solidify the distal layer forming solution. A hotplate was used as a heat source for heating.
<Manufacturing of Intermediate Layer>

Polylactic acid was dissolved in chloroform to prepare the intermediate layer forming solution. Then, the intermediate layer forming solution was injected into the mold in which the distal layer was formed by using an inkjet method. The mold to which the intermediate layer forming solution was supplied was heated at a temperature of 40° C. for a period of 10 minutes so as to dry and solidify the intermediate layer forming solution. A hotplate was used as a heat source for heating.
<Manufacturing of Proximal Layer>

Chitosan succinamide was dissolved in water to prepare the proximal layer forming solution. Rhodamine B was added to the proximal layer forming solution so as to have a 1% concentration relative to the distal layer forming solution. Then, the proximal layer forming solution was injected into the mold in which the distal layer and the intermediate layer were formed by using a spin coating method. The mold in which the proximal layer forming solution was supplied was heated at a temperature of 90° C. for a period of 10 minutes so as to dry and solidify the proximal layer forming solution. A hotplate was used as a heat source for heating.
<Removal of Microneedle>

The resultant product which was solidified was removed from the mold to obtain the microneedle of Example 1.
<Observation Result>

In the microscopic observation of the microneedle of Example 4, the distal layer and the proximal layer were clearly confirmed. In the microneedle of Example 1, a three layered structure made up of a stack of the layer containing chitosan succinamide, the layer containing polylactic acid and the layer containing chitosan succinamide were formed.

Reference Example 1

<Manufacturing of Mold>

An original plate for the microneedle was formed by micromachining a silicon substrate in the same manner as that of Example 1. Then, a mold made of nickel is formed by plating in the same manner as that of Example 1.
<Manufacturing of Distal Layer>

Chitosan succinamide was dissolved in water to prepare the distal layer forming solution. Evans Blue was added to the distal layer forming solution to have a 1% concentration relative to the distal layer forming solution. Then, the distal layer forming solution was injected into the recess of the mold by using an inkjet method. The mold in which the distal layer forming solution was supplied was heated at a temperature of 90° C. for a period of 10 minutes so as to dry and solidify the distal layer forming solution. A hotplate was used as a heat source for heating.

<Manufacturing of Proximal Layer>

Chitosan succinamide was dissolved in water to prepare the proximal layer forming solution. Rhodamine B was added to the proximal layer forming solution so as to have a 1% concentration relative to the distal layer forming solution. Then, the proximal layer forming solution was injected into the mold in which the distal layer was formed by using a spin coating method. The mold in which the proximal layer forming solution was supplied was heated at a temperature of 90° C. for a period of 10 minutes so as to dry and solidify the proximal layer forming solution. A hotplate was used as a heat source for heating.

<Removal of Microneedle>

The resultant product which was solidified was removed from the mold to obtain the microneedle of Example 1.

<Observation Result>

In the microscopic observation of the microneedle of Reference example 1, the distal layer and the proximal layer were clearly confirmed. However, it was found that the distal layer and the proximal layer were mixed at the interface between the distal layer and the proximal layer. In the magnifying observation, the extent of mixture of the distal layer and the proximal layer of the microneedle of Reference example 1 was significantly higher than that of the microneedle of Example 1.

Case 2

The microneedle of the present invention may have a two layer structure. Example 5 shows manufacturing of a two layered microneedle made up of the distal layer and the proximal layer. Further, Reference example 2 shows manufacturing of another example of the microneedle which includes the distal layer and the proximal layer both containing polymer that is water soluble and poorly soluble in oil.

Example 5

Manufacturing of Mold

An original plate for the microneedle was formed by micromachining a silicon substrate in the same manner as that of Example 1. Then, a mold made of nickel is formed by plating in the same manner as that of Example 1.

<Manufacturing of Distal Layer>

Hydroxypropyl cellulose was dissolved in water to prepare the distal layer forming solution. Evans Blue was added to the distal layer forming solution to have a 1% concentration relative to the distal layer forming solution. Then, the distal layer forming solution was injected into the recess of the mold by using an inkjet method. The mold in which the distal layer forming solution was supplied was heated at a temperature of 90° C. for a period of 10 minutes so as to dry and solidify the distal layer forming solution. A hotplate was used as a heat source for heating.

<Manufacturing of Proximal Layer>

Ethyl cellulose was dissolved in ethanol to prepare the proximal layer forming solution. Then, the proximal layer forming solution was injected into the mold in which the distal layer was formed by using an inkjet method. The mold in which the proximal layer forming solution was supplied was heated at a temperature of 40° C. for a period of 10 minutes so as to dry and solidify the proximal layer forming solution. A hotplate was used as a heat source for heating.

<Removal of Microneedle>

The resultant product which was solidified was removed from the mold to obtain the microneedle of Example 3.

<Observation Result>

In the microscopic observation of the microneedle of Example 3, the distal layer and the proximal layer were clearly confirmed. In the microneedle of Example 5, a two layered structure made up of a stack of the layer containing hydroxypropyl cellulose and the layer containing ethyl cellulose were formed.

Reference Example 2

<Manufacturing of Mold>

An original plate for the microneedle was formed by micromachining a silicon substrate in the same manner as that of Example 1. Then, a mold made of nickel is formed by plating in the same manner as that of Example 1.

<Manufacturing of Distal Layer>

Hydroxypropyl cellulose was dissolved in water to prepare the distal layer forming solution. Evans Blue was added to the distal layer forming solution to have a 1% concentration relative to the distal layer forming solution. Then, the distal layer forming solution was injected into the recess of the mold by using an inkjet method. The mold in which the distal layer forming solution was supplied was heated at a temperature of 90° C. for a period of 10 minutes so as to dry and solidify the distal layer forming solution. A hotplate was used as a heat source for heating.

<Manufacturing of Proximal Layer>

Carboxymethyl cellulose was dissolved in water to prepare the proximal layer forming solution. Then, the proximal layer forming solution was injected into the mold in which the distal layer was formed by using a spin coating method. The mold in which the proximal layer forming solution was supplied was heated at a temperature of 90° C. for a period of 10 minutes so as to dry and solidify the proximal layer forming solution. A hotplate was used as a heat source for heating.

<Removal of Microneedle>

The resultant product which was solidified was removed from the mold to obtain the microneedle of Reference example 2.

<Observation Result>

In the microscopic observation of the microneedle of Reference example 2, the distal layer and the proximal layer were clearly confirmed. In the microneedle of Reference example 2, a two layered structure made up of a stack of the layer containing hydroxypropyl cellulose and the layer containing carboxymethyl cellulose was formed. In the microneedle of Reference example 2, it was found that the distal layer and the proximal layer were mixed at the interface between the distal layer and the proximal layer. In the magnifying observation, the extent of mixture of the distal layer and the proximal layer of the microneedle of Reference example 2 was significantly higher than that of the microneedle of Example 3.

As described above, according to the present embodiment, the following advantages can be obtained.

(1) The polymer contained in the distal layer 23 is prevented from being eluted into a solvent that dissolves the intermediate layer 22. Accordingly, mixture of the polymers between the intermediate layer 22 and the distal layer 23 can be prevented.

(2) The polymer contained in the intermediate layer 22 is prevented from being eluted into a solvent that dissolves the proximal layer 21. Accordingly, mixture of the polymers between the proximal layer 21 and the intermediate layer 22 can be prevented.

(3) Since the intermediate layer 22 is interposed between the distal layer 23 and the proximal layer 21, the types or the content percentages of the water soluble polymers in each of layers may be easily varied.

(4) The water soluble polymer contained in the distal layer 23 and the proximal layer 21 is selected from a group consisting of carboxymethyl cellulose, hydroxypropyl cellulose, chitosan salt, chitosan succinamide, alginate, pullulan, dextran and chondroitin sulfate. Accordingly, when the microneedle is used to the human body, affinity between the material that is dissolved in the microneedle and the human body can be increased.

(5) The polymer soluble in oil contained in the intermediate layer 22 is ethyl cellulose. Since ethyl cellulose is least soluble in water, the polymer contained in the intermediate layer 22 can be appropriately prevented from being eluted into a solvent for forming the proximal layer 21. Further, as a solvent that dissolves the material for the intermediate layer 22, a solvent having less effect on the human body, such as ethanol, may be used.

(6) The substance to be delivered contained in the distal layer 23 can be prevented from being mixed along with the polymer into the intermediate layer 22. Accordingly, the substance to be delivered can be intensively disposed in the distal layer 23 that is inserted into the skin to the deepest position in the depth of insertion of the projection 12, and the substance to be delivered can be slowly released from a position deep in the skin.

The above embodiments can be modified as follows:

The projection 12 can be configured such that the substance to be delivered is supplied from the outside of the projection 12 and a hole may be formed in the projection 12 so as to allow the substance to be delivered into the body. In this case, the hole formed in the projection 12 may be a through hole that penetrates from the tip of the projection 12 to the lower surface of the substrate 11, or alternatively, the hole may not be a through hole. Further, regardless of whether the hole is formed or not, a recess may be formed around the projection 12 so as to guide the substance to be delivered to the target to be pierced.

The microneedle can be configured such that the substance to be delivered is supplied from the outside of the microneedle and a hole may be formed in the substrate 11 so as to allow guide the substance to be delivered to the projection 12. In this case, the hole formed in the substrate 11 may be a through hole that penetrates from the upper surface of the substrate 11 to the lower surface of the substrate 11, or alternatively, the hole may not be a through hole.

A support layer made of a material different from that of the substrate 11 may be provided on the lower surface of the substrate 11. For example, when the support layer is made of a material having a flexibility higher than that of the substrate 11, a material having a ductility higher than that of the substrate 11, or a material having a contraction coefficient smaller than that of the substrate 11, the flexure of the microneedle can be improved compared to the microneedle supported by a hard support member. Further, the microneedle can be stocked in a state wound in a roll. Moreover, when the support layer per se is made of a soft material, it is possible to prevent the tip of the projection 12 from being deformed when a plurality of microneedles are stacked.

Both the proximal layer 21 and the distal layer 23 may include the substance to be delivered. Alternatively, only the proximal layer 21 may include the substance to be delivered.

Whether the substance to be delivered is supplied to the microneedle from the outside of the microneedle or not depends on the application of use of the microneedle. Further, water soluble polymer may serve as the substance to be delivered. In the configuration in which the substance to be delivered is supplied from the outside of the microneedle or water soluble polymer serves as the substance to be delivered, the proximal layer 21 and the distal layer 23 do not need to contain the substance to be delivered beside the water soluble polymer.

The distal layer 23 may contain a plurality of water soluble polymers selected from a group consisting of carboxymethyl cellulose, hydroxypropyl cellulose, chitosan salt, chitosan succinamide, alginate, pullulan, dextran and chondroitin sulfate. Further, the distal layer 23 may contain other water soluble polymers than those described above. In other words, the polymer contained in the distal layer 23 may be any polymer which is water soluble and poorly soluble in oil.

The intermediate layer 22 may contain polymers other than ethyl cellulose. Further, the polymer contained in the intermediate layer 22 may be oil soluble and water soluble. With this configuration, the advantage of the above (1) can also be obtained.

The proximal layer 21 may contain a plurality of water soluble polymers selected from a group consisting of carboxymethyl cellulose, hydroxypropyl cellulose, chitosan salt, chitosan succinamide, alginate, pullulan, dextran and chondroitin sulfate. Further, the proximal layer 21 may contain other water soluble polymers than those described above. With this configuration, the advantage of the above (2) can also be obtained as long as the polymer contained in the intermediate layer 22 is soluble in oil and poorly soluble in water.

The microneedle may be formed of four or more layers. In a configuration in which the layers containing polymer soluble in water and poorly soluble in oil and the layers containing polymer soluble in oil and poorly soluble in water are alternatively stacked, the polymer contained in an earlier formed layer is not easily dissolved in the solvent that dissolves a later formed layer. Accordingly, the polymer contained in each of the layers is prevented from being mixed into the adjacent layer.

The microneedle may contain only two layer, that is, a layer containing polymer soluble in water and poorly soluble in oil and a layer containing polymer soluble in oil. The advantage of the above (1) can be obtained as long as the microneedle is configured such that the layer containing polymer soluble in oil and the layer containing polymer soluble in water and poorly soluble in oil are adjacent to each other. For example, when the projection 12 is a layer containing polymer soluble in water and poorly soluble in oil and the substrate 11 is a layer containing polymer soluble in oil, the substance to be delivered contained in the projection 12 is prevented from being mixed into the substrate 11, thereby preventing use of a substance which is unnecessary to be delivered.

In recent years, microneedles having a two layer structure have been developed. Two layers which constitute the two layer structure are stacked in a direction in which the projection extends, and the types or content percentages of the water soluble polymers in each of two layers are different.

In a manufacturing process of a microneedle having a two layer structure, a solution for forming the first layer is supplied and solidified. Then, a solution for forming the second layer is supplied and solidified. In so doing, since the solution for forming the second layer is supplied on the solidified first layer, the water soluble polymer contained in the solidified first layer may be eluted into the solution for forming the second layer. As a result, the types or content percentages of the water soluble polymers contained in each of two layers may vary, which may compromise the function that should be necessary for the two layer structure.

Further, migration of water soluble polymers across the layers occurs not only in the manufacturing process of a microneedle, but also, for example, in the case where water that dissolves the water soluble polymer comes into contact with the microneedle.

An object of the technique of the present disclosure is to provide a microneedle that is capable of preventing the polymers contained in each of layers from being mixed into other layers, and provide a method for manufacturing a microneedle.

An aspect of a microneedle according to the disclosure includes a substrate, and a plurality of projections which extend from a surface of the substrate, wherein each of the projections is made up of a plurality of layers separated from each other in a direction in which the projection extends. The plurality of layers include a first layer which contains polymer that is soluble in water and poorly soluble in oil and a second layer which contains polymer that is soluble in oil, and the first layer and the second layer are adjacent to each other and are arranged in the order of the first layer and the second layer from the projection to the substrate.

Another aspect of a method for manufacturing a microneedle according to the disclosure which includes a substrate, and a plurality of projections which extend from a surface of the substrate, wherein each of the projections is made up of a plurality of layers separated from each other in a direction in which the projection extends, the method comprising: forming a first layer by supplying a solution in which a material containing polymer that is soluble in water and poorly soluble in oil is dissolved in water into a mold and solidifying the supplied solution, and forming a second layer by supplying a solution containing a material which contains polymer that is soluble in oil is dissolved in organic solvent onto the first layer in the mold and solidifying the supplied solution.

According to the above aspect, the polymer contained in the first layer which is a layer located close to the tip of the projection is poorly soluble in oil, while the polymer contained in the second layer which is a layer located away from the tip of the projection is soluble in oil. Accordingly, the polymer contained in the first layer can be prevented from being eluted into a solvent that dissolves the second layer.

In the above microneedle, it is preferable that the polymer contained in the second layer is soluble in oil and poorly soluble in water.

In the above microneedle, it is preferable that the plurality of layers further include a third layer which contains polymer that is soluble in water, and the second layer is interposed between the first layer and the third layer.

According to the above aspect, the polymer contained in the second layer, of the second layer and the third layer adjacent to each other, which is a layer located close to the tip of the projection is poorly soluble in water. On the other hand, the polymer contained in the third layer which is a layer located away from the tip of the projection is soluble in water. Accordingly, the polymer contained in the second layer can be prevented from being eluted into a solvent that dissolves the third layer.

In the above microneedle, it is preferable that the polymer contained in the first layer includes at least one selected from a group consisting of carboxymethyl cellulose, hydroxypropyl cellulose, chitosan salt, chitosan succinamide, alginate, pullulan, dextran and chondroitin sulfate.

According to the above aspect, since the polymer which is less soluble in organic solvent is used as the polymer contained in the first layer, the polymer contained in the first layer can be appropriately prevented from being eluted into a solvent that dissolves the second layer.

In the above microneedle, it is preferable that the polymer contained in the second layer is ethyl cellulose.

According to the above aspect, the polymer contained in the second layer is ethyl cellulose. Accordingly, a solvent having less effect on the human body, such as ethanol, may be used as a solvent in which the material of the second layer dissolves. Further, when the microneedle includes the third layer, the polymer contained in the second layer can be appropriately prevented from being eluted into a solvent for forming the third layer since ethyl cellulose is least soluble in water. Propyl cellulose may be used instead of ethyl cellulose. Polylactic acid may be used instead of ethyl cellulose.

In the above microneedle, it is preferable that the projection is configured to be capable of piercing a target, and the first layer further includes a subject to be delivered to an outside of the projection.

According to the above aspect, the substance to be delivered contained in the first layer can be prevented from being mixed along with the polymer into the second layer. Accordingly, the substance to be delivered can be intensively disposed in the first layer that is inserted into the skin deeper than the second layer.

In the above method for manufacturing a microneedle, it is preferable that the polymer contained in the second layer is soluble in oil and poorly soluble in water.

Preferably, the manufacturing method further includes forming a third layer by supplying a solution in which a material which contains polymer that is soluble in water and poorly soluble in oil dissolved in water onto the second layer in the mold and solidifying the supplied solution.

According to the technique of the present disclosure, in a microneedle having a multi-layer structure, the polymer contained in each of the layers can be prevented from being mixed into other layers.

REFERENCE SIGNS LIST 11 substrate, 12 projection, 21 proximal layer, 22 intermediate layer, 23 distal layer, 31 mold Obviously, numerous modifications and variations of the present invention are possible in light of the above teachings. It is therefore to be understood that within the scope of the appended claims, the invention may be practiced otherwise than as specifically described herein.

What is claimed is:

1. A microneedle, comprising:
a substrate; and
a plurality of projections extending from a surface of the substrate,
wherein each of the plurality of projections comprises a plurality of layers stacked from the surface of the substrate to a tip of each of the plurality of projections such that the plurality of layers includes a first layer forming a distal layer including the tip and comprising an active substance and a polymer, the polymer comprising at least one selected from the group consisting of carboxymethyl cellulose, hydroxypropyl cellulose, chitosan salt, chitosan succinamide, alginate, pullulan, dextran and chondroitin sulfate, a second layer forming an intermediate layer on which the distal layer is formed in contact with the intermediate layer and comprising a polymer, the polymer comprising at least one selected from the group consisting of ethyl cellulose, propyl cellulose and polylactic acid, and a third layer forming a proximal layer on which the intermediate layer is formed in contact with the proximal layer and comprising a polymer soluble in water, and the plurality of layers is formed such that the second layer has a thickness that is smaller than a thickness of the first layer and a thickness of the third layer.

2. The microneedle according to claim 1, wherein the plurality of layers is formed such that the third layer includes proximal ends of each of the plurality of projections.

3. The microneedle according to claim 2, wherein the polymer in the second layer is ethyl cellulose.

4. The microneedle according to claim 3, wherein the polymer in the first layer is chitosan succinamide.

5. The microneedle according to claim 4, wherein the polymer in the third layer is chitosan succinamide.

6. The microneedle according to claim 2, wherein the polymer in the second layer is propyl cellulose.

7. The microneedle according to claim 2, wherein the polymer in the second layer is polylactic acid.

8. The microneedle according to claim 1, wherein the polymer in the first layer is chondroitin sulfate.

9. The microneedle according to claim 8, wherein the polymer in the second layer is ethyl cellulose.

10. The microneedle according to claim 8, wherein the polymer in the second layer is propyl cellulose.

11. The microneedle according to claim 8, wherein the polymer in the second layer is polylactic acid.

12. The microneedle according to claim 1, wherein the active substance includes one of a pharmacological active agent and a cosmetic composition.

13. The microneedle according to claim 1, wherein the polymer in the second layer is ethyl cellulose.

14. The microneedle according to claim 1, wherein the polymer in the second layer is propyl cellulose.

15. The microneedle according to claim 1, wherein the polymer in the second layer is polylactic acid.

16. The microneedle according to claim 1, wherein each of the plurality of projections are configured to pierce a target.

17. The microneedle according to claim 1, wherein the polymer in the first layer is chitosan succinamide.

* * * * *